US012799468B2

(12) United States Patent
Loftie-Eaton et al.

(10) Patent No.: US 12,799,468 B2
(45) Date of Patent: Nov. 17, 2026

(54) VARIANTS OF ENDONUCLEASE V AND USES THEREOF

(71) Applicant: DNA Script, Le Kremlin-Bicêtre (FR)

(72) Inventors: Wesley Loftie-Eaton, Le Kremlin-Bicêtre (FR); Tillmann Heinisch, Le Kremlin-Bicêtre (FR); Mikhael Soskine, Franconville (FR); Elise Champion, Paris (FR); Xavier Godron, Le Kremlin-Bicêtre (FR); Thomas Ybert, Paris (FR)

(73) Assignee: DNA Script, Le Kremlin-Bicêtre (FR)

( * ) Notice: Subject to any disclaimer, the term of this patent is extended or adjusted under 35 U.S.C. 154(b) by 697 days.

(21) Appl. No.: 18/033,787

(22) PCT Filed: Oct. 21, 2021

(86) PCT No.: PCT/EP2021/079254

§ 371 (c)(1),
(2) Date: Apr. 25, 2023

(87) PCT Pub. No.: WO2022/090057

PCT Pub. Date: May 5, 2022

(65) Prior Publication Data

US 2023/0416708 A1 Dec. 28, 2023

(30) Foreign Application Priority Data

Oct. 26, 2020 (EP) .................................... 20306277

(51) Int. Cl.
*C12N 9/22* (2006.01)
*C12N 9/96* (2006.01)

(52) U.S. Cl.
CPC ................ *C12N 9/22* (2013.01); *C12N 9/96* (2013.01); *C12Y 301/27008* (2013.01)

(58) Field of Classification Search
CPC ..... C12N 9/22; C12N 9/96; C12Y 301/27008
See application file for complete search history.

(56) References Cited

U.S. PATENT DOCUMENTS 5,808,045 A 9/1998 Hiatt et al.
6,020,141 A 2/2000 Pantoliano et al.
8,808,988 B2 8/2014 Zhao et al.
10,435,676 B2 10/2019 Champion et al.
10,752,887 B2 8/2020 Champion et al.
11,208,637 B2 12/2021 Champion et al.
11,390,856 B2 7/2022 Ybert et al.
11,859,217 B2 1/2024 Champion et al.
12,065,461 B2 8/2024 Sarac et al.
12,071,638 B2 8/2024 Champion et al.
12,173,333 B2 12/2024 Ybert et al.
12,286,652 B2 4/2025 Champion et al.
12,371,680 B2 7/2025 Champion et al.
12,377,397 B2 8/2025 Martin et al.
12,421,628 B2 9/2025 Horgan et al.
12,428,668 B2 9/2025 Godron et al.
2014/0093878 A1 4/2014 Nelson et al.
2020/0002690 A1 1/2020 Ybert et al.
2022/0315970 A1 10/2022 Horgan
2022/0403434 A1 12/2022 Heinisch et al.
2022/0403435 A1 12/2022 Horgan et al.
2022/0403436 A1 12/2022 Horgan et al.
2022/0411840 A1 12/2022 Champion et al.
2023/0062303 A1 3/2023 Champion et al.
2023/0089448 A1 3/2023 Horgan et al.
2023/0159903 A1 5/2023 Soskine et al.
2023/0167421 A1 6/2023 Ybert et al.
2023/0203553 A1 6/2023 Ybert
2023/0313255 A1 10/2023 Horgan et al.
2024/0052391 A1 2/2024 Godron et al.
2024/0093256 A1 3/2024 Soskine et al.
2024/0124855 A1 4/2024 Ybert et al.
2024/0279700 A1 8/2024 Horgan
2024/0352443 A1 10/2024 Creton et al.
2025/0002879 A1 1/2025 Mchale et al.
2025/0034532 A1 1/2025 Mchale et al.
2025/0205700 A1 6/2025 Lachaize et al.
2025/0215617 A1 7/2025 Horgan et al.
2025/0223575 A1 7/2025 Champion et al.
2025/0283132 A1 9/2025 De et al.

FOREIGN PATENT DOCUMENTS

WO 91/06678 A1 5/1991
WO 2020/099451 A1 5/2020
WO 2020/165137 A1 8/2020

OTHER PUBLICATIONS

Arimizu et al., GenBank accession No. GDS84708, Apr. 16, 2019.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Altschul, S. F. et al. (2005). "Protein Database Searches Using Compositionally Adjusted Substitution Matrices," FEBS J. 272:5101-5109.
Altschul, S.F. et al. (1997). "Gapped BLAST and PSI-BLAST: A new Generation of Protein Database Search Programs," Nucleic Acids Research 25(17):3389-3402.
Ericsson, U.B. et al. (2006, e-pub. Aug. 10, 2006). "Thermofluor-Based High-Throughput Stability Optimization of Proteins for Structural Studies," Analytical Biochemistry 357:289-298.

(Continued)

*Primary Examiner* — Delia M Ramirez
(74) *Attorney, Agent, or Firm* — MORRISON & FOERSTER LLP

(57) ABSTRACT

The present invention relates to novel polypeptides having an endonuclease V activity, and uses thereof.

10 Claims, 3 Drawing Sheets

Specification includes a Sequence Listing.

(56) References Cited

OTHER PUBLICATIONS

Genbank Accession No. NC_000913.3, last updated Mar. 9, 2022, "*Escherichia coli* Str. K-12 Substr. Mg655, Complete Genome," NCBI, 3 pages.
Hebditch, M. et al. (2017, e-pub. Sep. 29, 2017). "Sequence Composition Predicts Immunoglobulin Superfamily Members That Could Share the Intrinsically Disordered Properties of Antibody CH1 Domains," Scientific Reports 7:12404:1-9.
Huynh, K. et al. (2015). "Analysis of Protein Stability and Ligand Interactions by Thermal Shift Assay," Curr. Protocol. Protein Science 79:28.9.1-28.9.14.
International Preliminary Report on Patentablity issued on May 2, 2023, for PCT Application No. PCT/EP2021/079254, filed on Oct. 21, 2021, 7 pages.
International Search Report and Written Opinion mailed on Feb. 18, 2022, for PCT Application No. PCT/EP2021/079254, filed on Oct. 21, 2021, 11 pages.
Ke, S-H. et al. (1997). "Rapid and Efficient Site-Directed Mutagenesis by Single-Tube 'Megaprimer' PCR Method," Nucleic Acids Research 25(16):3371-3372.
Needleman, S.B. et al. (1970). "A General Method Applicable to the Search for Similarities in the Amino Acid Sequence of Two Proteins," J. Mol. Biol. 48:443-453.
Niesen, F.H. et al. (2007). "The Use of Differential Scanning Fluorimetry to Detect Ligand Interactions That Promote Protein Stability," Nature Protocols 2(9):2212-2221.
Nyaga, S.G. et al. (Jan. 1, 1997). "Role of Specific Amino Acid Residues in T4 Endonuclease V That Alter Nontarget DNA Binding," Biochemistry 36(14):4080-4088.
Pantoliano, M.W. et al. (2001). "High-Density Miniaturized Thermal Shift Assays as a General Strategy for Drug Discovery," Journal of Biomolecular Screening 6(6):429-440.
Smith, T.F. et al. (1981). "Identification of Common Molecular Subsequence," J. Mol. Biol. 147:195-197.
UNIPROT. (May 21, 2019). "Endonuclease V from *E. coli*," Accession No. UNIPARC: UPI001CB6756, 2 pages.
Zhao, H. et al. (2006, e-pub. Nov. 22, 2006). "In Vitro 'Sexual' Evolution Through the PCR-Based Staggered Extension Process (StEP)," Nature Protocols 1(4):1865-1871.
U.S. Appl. No. 18/993,240, Title: Method of Purifying Solution Comprising Polynucleotide, filed Jan. 10, 2025, by Mouaadh Kellal (A U.S. Patent Application is not submitted herewith pursuant to the waiver of 37 C.F.R. § 1.98(a)(2)(iii) issued by the Office on Sep. 21, 2004.).
U.S. Appl. No. 19/122,511, Title: Methods and Products for Removal of Uracil Containing Polynucleotides, filed Apr. 18, 2025, by Mikhael Soskine (A U.S. Patent Application is not submitted herewith pursuant to the waiver of 37 C.F.R. § 1.98(a)(2)(iii) issued by the Office on Sep. 21, 2004.).
U.S. Appl. No. 19/132,344, Title: Variants of Poly(A) Polymerase and Uses Thereof, filed May 22, 2025, by Tillmann Heinisch (A U.S. Patent Application is not submitted herewith pursuant to the waiver of 37 C.F.R. § 1.98(a)(2)(iii) issued by the Office on Sep. 21, 2004.).
U.S. Appl. No. 19/136,668, Title: In Vitro Enzymatical RNA Synthesis, filed Jun. 6, 2025, by Tillmann Heinisch (A U.S. Patent Application is not submitted herewith pursuant to the waiver of 37 C.F.R. § 1.98(a)(2)(iii) issued by the Office on Sep. 21, 2004.).
U.S. Appl. No. 19/143,773, Title: Variable Viscosity Inks for Inkjet Delivery of Enzyme Reagents, filed Jun. 26, 2025, by Adrian Horgan (A U.S. Patent Application is not submitted herewith pursuant to the waiver of 37 C.F.R. § 1.98(a)(2)(iii) issued by the Office on Sep. 21, 2004.).
U.S. Appl. No. 19/144,006, Title: Heat Treatment Means for Printing Device of an Enzymatic Synthesis Apparatus, filed Jun. 27, 2025, by Adrian Horgan (A U.S. Patent Application is not submitted herewith pursuant to the waiver of 37 C.F.R. § 1.98(a)(2)(iii) issued by the Office on Sep. 21, 2004.).
U.S. Appl. No. 19/144,778, Title: Methods for Obtaining Correctly Assembled Nucleic Acids, filed Jun. 30, 2025, by Jeffrey Jeddeloh (A U.S. Patent Application is not submitted herewith pursuant to the waiver of 37 C.F.R. § 1.98(a)(2)(iii) issued by the Office on Sep. 21, 2004.).
U.S. Appl. No. 19/148,244, Title: Scarless Template-Free Enzymatic Synthesis of Polynucleotides, filed Jul. 15, 2025, by Adrian Horgan (A U.S. Patent Application is not submitted herewith pursuant to the waiver of 37 C.F.R. § 1.98(a)(2)(iii) issued by the Office on Sep. 21, 2004.).
U.S. Appl. No. 19/148,524, Title: Inkjet-Assisted Enzymatic Nucleic Acid Synthesis, filed Jul. 16, 2025, by Nicolas Moghaddam (A U.S. Patent Application is not submitted herewith pursuant to the waiver of 37 C.F.R. § 1.98(a)(2)(iii) issued by the Office on Sep. 21, 2004.).
U.S. Appl. No. 19/150,746, Title: Enzymatic Synthesis of Polynucleotide Probes, filed Jul. 24, 2025, by Thomas Ybert (A U.S. Patent Application is not submitted herewith pursuant to the waiver of 37 C.F.R. § 1.98(a)(2)(iii) issued by the Office on Sep. 21, 2004.).
U.S. Appl. No. 19/241,170, Title: Systems, Apparatus and Kits for Enzymatic Polynucleotide Synthesis, filed Jun. 17, 2025, by Carl Martin (A U.S. Patent Application is not submitted herewith pursuant to the waiver of 37 C.F.R. § 1.98(a)(2)(iii) issued by the Office on Sep. 21, 2004.).

* cited by examiner

VARIANTS OF ENDONUCLEASE V AND USES THEREOF

CROSS REFERENCE TO RELATED APPLICATIONS

This application is a national stage application under 35 U.S.C. § 371 of International Application No. PCT/EP2021/079254, filed internationally on Oct. 21, 2021, which claims priority benefit to EP Application No. EP20306277, filed Oct. 26, 2020.

The present invention relates to novel polypeptides having an endonuclease V activity. More particularly, the present invention relates to variants of Endonuclease V of *E. coli*, which exhibit improved properties as compared to parent Endonuclease V. The variants of the present invention are particularly well suited for rapid site-specific cleavage of single- or double-stranded DNA and RNA containing one or more deoxyinosine bases, where the deoxyinosine-containing nucleic acids are either conjugated to a solid support or free in solution. Variants of the present invention cleave efficiently whether or not a moiety, such as a fluorophore or biotin, is attached to the nucleotide distal of the cleavage site relative to the solid support.

BACKGROUND OF THE INVENTION

Endonuclease V (herein after referred as Endo V), also called deoxyinosine 3' endonuclease, is a DNA repair enzyme that recognizes DNA containing deoxyinosine (a deamination product of a deoxyadenosine, also referred as inosine and hypoxanthine) residues. Endo V primarily cleaves the second and third phosphodiester bond 3' to an inosine residue in the same strand, leaving a nick with a 3'-hydroxyl and a 5'-phosphate.

Endo V enzymes are useful in a wide variety of biochemical fields, including analysis, detection, degradation, synthesis and modification of nucleic acid molecules. The Endo V isolated from *E. coli* has been used to cleave and release single stranded DNA that has otherwise been conjugated to solid support, e.g. Creton, International patent publication WO2020/165137. While the Endo V produced by *E. coli* exhibits high specificity in comparison to other Endo Vs, such as that produced by the thermophilic organism *Thermotoga maritima*, it lacks (thermo)stability. Since Endo V is currently used in processes under conditions (e.g. high temperature, high salt, prolonged periods of time at non-reducing conditions, etc.) outside those for optimal enzymatic activity, there is thus a need for novel enzymes with Endo V activity, which may be used under severe conditions with greater efficiency than those currently available.

SUMMARY OF THE INVENTION

By working on Endo V of *E. coli*, to develop novel enzymes having improved activity as compared to currently available Endo V, the inventors have identified specific amino acid residues which may be substituted for improving the overall properties of the enzyme. The inventors have more particularly discovered that residues such as C136, C169, C192, K133, K138, K155, K194 and/or D206H may be advantageously substituted to improve the residual activity of the enzyme, particularly after it has been exposed to thermal stress in the absence of stabilizing agents such as bovine serum albumin (BSA) or to antioxidants such as tris(2-carboxyethyl)phosphine (TCEP), and dithiothreitol (DTT). Interestingly, the inventors have discovered that combinations of substitutions at C169 with K133, K138, K155, K194 and/or D206 further improves the solubility and/or the thermostability of the enzyme. The inventors have thus developed particular variants of EndoV of *E. coli* that exhibit increased stability, longevity, and/or thermostability of the enzyme, as well as improved cleavage kinetics as compared to the parent Endo V.

It is thus the purpose of the present invention to provide an endonuclease V variant which (i) has at least 75%, 80%, 85%, 90%, 95% or 99% identity to the full length amino acid sequence set forth in SEQ ID No 1, (ii) has one or more amino acid substitutions as compared to SEQ ID No 1 at position(s) selected from C136, C169 and C192, wherein the positions are numbered by reference to the amino acid sequence set forth in SEQ ID No 1, (iii) has a deoxyinosine-specific nucleic acid cleavage activity and (iv) exhibits improved residual activity under non-reducing condition as compared to endonuclease V of SEQ ID No 1.

Preferably, the variant of the present invention comprises at least one substitution selected from C136W, C169Q/G/L/P/W and C192L, preferably selected from C169Q/G/L/P, more preferably selected from C169Q/G/P, even more preferably C169Q.

In some embodiments, the present invention further provides a nucleic acid encoding an Endonuclease V of the present invention, expression cassette or vector comprising said nucleic acid.

In some embodiments, the present invention provides a method of producing an endonuclease V comprising:

(a) culturing the host cell of the present invention under conditions suitable to express the nucleic acid encoding the endonuclease V; and optionally (b) recovering said endonuclease V from the cell culture.

In further embodiments, the present invention provides a method for nucleic acid cleavage, which comprises the use of a variant of endonuclease V according to the present invention, particularly, for cleaving a single stranded nucleic acid conjugated to a solid support.

DETAILED DESCRIPTION OF THE INVENTION

Definitions

Figure 1:
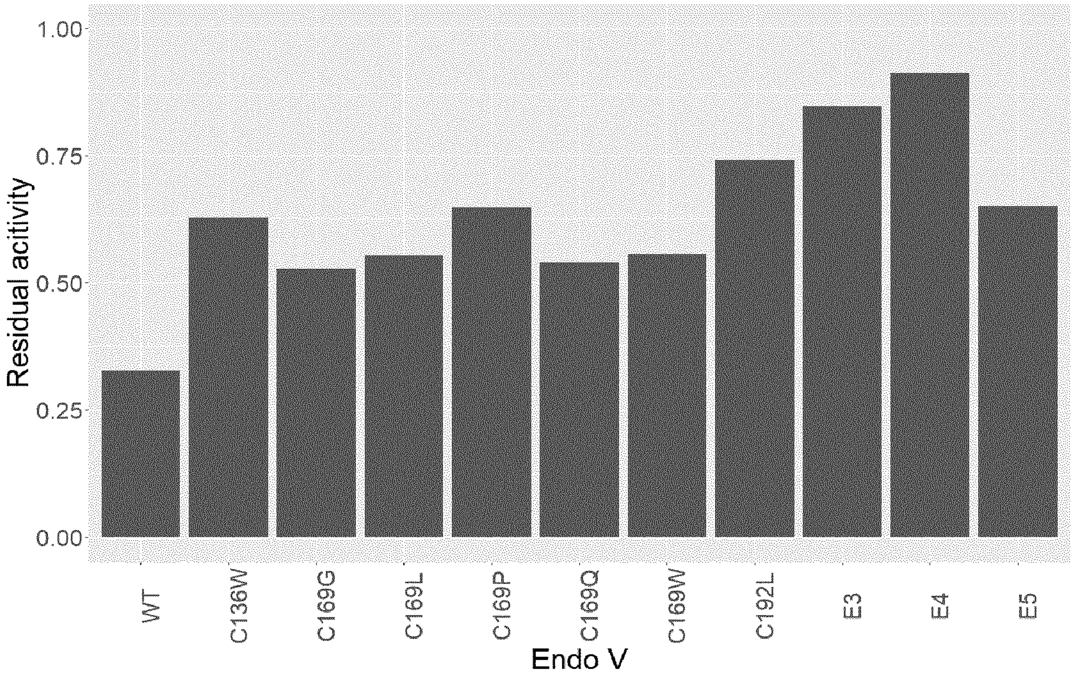
FIG. 1 is a graph showing the residual activity for Wild-type Endo V and various variants according to the present invention after the enzymes were incubated for 6 hours at 42° C. vs 4° C.

The present disclosure will be best understood by reference to the following definitions.

Herein, the terms "peptide", "polypeptide", "protein", "enzyme" refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

The terms "wild-type enzyme", "WT enzyme" or "parent enzyme" are used interchangeably and refer to the non-mutated version of an enzyme as it appears naturally. In the present case, the parent enzyme refers to the Endo V isolated from *E. coli* having the amino acid sequence as set forth in SEQ ID NO:1.

Accordingly, the terms "mutant" and "variant" may be used interchangeably to refer to polypeptides derived from SEQ ID NO:1 and comprising a modification or an alteration, i.e., a substitution, insertion, and/or deletion, at one or more (e.g., several) positions and having an Endo V activity. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: Y167R denotes that amino acid residue Tyrosine (Y) at position 167 of the parent sequence is changed to an Arginine (R). Y167V/I/M denotes that amino acid residue Tyrosine (Y) at position 167 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

Unless otherwise specified, the positions disclosed in the present application are numbered by reference to the amino acid sequence set forth in SEQ ID NO:1.

As used herein, the term "nucleic acid", "nucleic sequence," "polynucleotide", "oligonucleotide" and "nucleotide sequence" are used interchangeably and refer to a sequence of deoxyribonucleotides and/or ribonucleotides. The nucleic acids can be DNA (cDNA or gDNA), RNA, or a mixture of the two. It can be in single stranded form or in duplex form or a mixture of the two. It can be of recombinant, artificial and/or synthetic origin and it can comprise modified nucleotides, comprising for example a modified bond, a modified purine or pyrimidine base, or a modified sugar.

As used herein, the term "sequence identity" or "identity" refers to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as blast.ncbi.nlm.nih.gov/or www.ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e., Scoring matrix=BLOSUM62, Gap open=10, Gap extend=0.5, End gap penalty=false, End gap open=10 and End gap extend=0.5.

The term "recombinant" refers to a nucleic acid construct, a vector, a polypeptide or a cell produced by genetic engineering.

The term "expression", as used herein, refers to any step involved in the production of a polypeptide including, but not being limited to, transcription, post-transcriptional modification, translation, post-translational modification, and secretion.

The term "expression cassette" denotes a nucleic acid construct comprising a coding region, i.e. a nucleic acid of the invention, and a regulatory region, i.e. comprising one or more control sequences, operably linked.

As used herein, the term "expression vector" means a DNA or RNA molecule that comprises an expression cassette of the invention. Preferably, the expression vector is a linear or circular double stranded DNA molecule.

Novel Variants of Endo V

The inventors have designed new variants of Endo V derived from *E. coli* that exhibit a greater overall activity as compared to the parent enzyme. More particularly, the variants of the present invention exhibit improved cleavage activity compared to the Endo V of SEQ ID NO:1.

Advantageously, the variants may also exhibit an improved (thermo)stability, improved solubility, etc., which directly or indirectly impact the overall activity of the enzyme. The Endo V of the present invention are particularly suited for rapid site-specific cleavage of an oligonucleotide containing one or more deoxyinosine bases, where the deoxyinosine-containing nucleic acids are conjugated to a solid support and which may or may not have a modification such as a fluorophore or biotin attached to the nucleotide base proximal to the cleavage site, which is second phosphodiester bond 3' to the deoxyinosine.

The variants of Endo V of the invention may comprise one or several modifications as disclosed below.

According to the invention, the endonuclease V variant (i) has at least 75%, 80%, 85%, 90%, 95% or 99% identity to the full length amino acid sequence set forth in SEQ ID No 1, (ii) has one or more amino acid substitutions as compared to SEQ ID No 1 at position(s) selected from C136, C169 and C192, wherein the positions are numbered by reference to the amino acid sequence set forth in SEQ ID No 1, (iii) has a deoxyinosine-specific nucleic acid cleavage activity, and (iv) exhibits improved overall activity as compared to endonuclease V of SEQ ID No 1.

According to the invention, the targeted amino acid(s) may be replaced by any one of the 19 other amino acids.

Within the context of the present invention, the "overall activity" refers to the cleavage activity of the enzyme, i.e. the ability of the enzyme to recognize a deoxyinosine (dI) residue contained in nucleic acid molecules and to cleave at the second phosphodiester bond 3' of the recognized base. Within the context of the present invention, the "residual activity" refers to enzyme activity that remains after exposure of the enzyme to conditions that negatively impact enzyme structure/activity such as high temperature, pH extremes, non-reducing conditions, etc.

The activity of an enzyme may be evaluated by the one skilled in the art, according to methods known per se in the art. For instance, the activity can be assessed by the measurement of the specific Endo V activity rate, the measurement of the specific cleavage activity rate, or the like. For instance, a standard DNA sample may be dissolved in an adequate buffer, and the Endo V enzyme is added thereto at an adequate temperature (e.g., 37° C.). Whether or not the nucleic acid is cleaved into smaller subunits may then be examined by visualizing or quantifying the smaller subunits by electrophoretic techniques (e.g. agarose gel electrophoresis), changes in fluorescence resonance energy transfer (e.g. due to the separation of FAM and TAMRA fluorophores) or an increase in absorbance of the resulting solution at the wavelength of 260 nm within a given period of time (e.g., 1 minute) after the addition of the enzyme. The presence of endonuclease residual activity can be determined on the basis of such increase.

Within the context of the invention, the terms "increased overall activity" or "improved overall activity" or "greater overall activity" indicate an increased ability of the enzyme to cleave and release a nucleic acid molecule as compared to the Endo V of SEQ ID No 1, submitted to identical conditions of reaction (e.g. temperature, concentration, pH, addition of stabilizing agents, etc.). Such an increase is typically of about 1-fold, 2-fold, 3-fold, 4-fold, 5-fold, or more. Particularly, the Endo V variant has a cleavage activity at least 10% greater than the cleavage activity of the Endo V of SEQ ID No 1, preferably at least 15%, 20%, 25%, 30%, 40%, 50%, 60%, 70%, 80%, 90%, 100% or greater.

Interestingly, the variants of the present invention exhibit an increased residual Endo V activity as compared to parent Endo V in absence of reducing agent. As used herein, the term "reducing agent" refers to agent that has capability to reduce disulfides to mercaptans. Suitable reducing agents may be selected from bovine serum albumin (BSA) or antioxidants such as tris(2-carboxyethyl)phosphine (TCEP) or dithiothreitol (DTT). In a particular embodiment, the variants of the present invention further (v) exhibit improved residual activity after incubation in a buffer lacking any stabilizing agents such as BSA or TCEP or DTT, particularly for 2, 4, 6 or more hours at temperatures such as 42° C. as compared to endonuclease V of SEQ ID No 1.

The increased residual activity may be measured by incubating the enzyme in a reaction buffer without substrate, with or without BSA and TCEP, for 6 hours at 4° C. and 42° C., prior to measuring cleavage of a resin-linked, fluorescently labelled deoxyinosine-containing oligonucleotide substrate such as those in SEQ ID No 3, 4 and 5, for example. After 6 hours of incubation, the parent enzyme shows diminished activity after being incubated at 42° C. relative to the control incubated at 4° C. and in the absence of BSA and TCEP, while the variants of the invention don't.

In a particular embodiment, the Endo V variant comprises at least one substitution selected from C136W, C169Q/G/L/P/W and C192L.

Preferably, the Endo V variant of the invention does not comprise the substitution C136A/E/Q/T/V C169E/P/W or C192G/I/P/S/T/W.

In a particular embodiment, the Endo V variant comprises at least one substitution selected from C169Q/G/L/P, preferably selected from C169Q/G/L, more preferably C169Q. Interestingly, variants that comprises the substitution C169G, G169L or G169P are more stable enzymes when challenged at 42° C. for 6 h in the absence of a protective agent such as 0.5 mM TCEP or 0.033 mg·ml$^{-1}$ BSA compared to parent Endo V (i.e. the residual activity of these variants is higher than the residual activity of the parent Endo V).

Preferably, the variant comprises at least the substitution C169Q.

In another particular embodiment, the Endo V variant comprises at least one substitution selected from K133T, K138D/Y, K155G/N, K194R and D206H, preferably selected from K133T, K138D and K194R.

In addition to the beneficial effects on stability of the variants in absence of reducing agents, the below listed substitutions also improve solubility and/or thermostability and/or substrate affinity ($K_m$) and/or catalytic turnover ($K_{cat}$), (extrapolated from Michaelis-Menten enzyme kinetic assays as described by Menten et al., 2011) of the variants.

The solubility may be measured as a decrease in the percentage of protein lost due to precipitation after 4 or more days at 4° C. in a buffer without a cryoprotectant such glycerol (propane-1,2,3-triol).

The thermostability may be measured as the change in melting temperature by means of a thermal shift assay.

In some embodiments, a heat stable endonuclease V is preferred. For example, in a nucleic acid assay, where thermal denaturation (either partial or full denaturation) of a target DNA is performed, a heat stable endonuclease V may be preferred. Interestingly, the inventors have identified specific amino acid residues of SEQ ID NO:1 that may be substituted in order to increase the thermostability of the corresponding variants compared to the parent enzyme.

An increased thermostability means that the melting temperature (Tm) of the variant is at least 1° C., 2° C., 3° C., 4° C., 5° C., 6° C., 7° C., 8° C., 9° C., 10° C. or more, higher than the melting temperature of the parent enzyme, particularly 1° C. to 3° higher. Such an increase is typically of about 5, 10, 15, 20, 25% or more. In a particular embodiment, the melting temperature of the variant of the invention is within 30° C. and 60° C., particularly within 45 and 65° C., 50° C. and 60° C., 52° C. and 58° C., 54° C. and 56° C. In a particular embodiment, the melting temperature of the variant of the invention is 54° C., 56° C., 58° C.

In a particular embodiment, the Endo V variant further exhibits an improved solubility.

Enzymes, like other compounds, exhibit an upper limit of solubility in a given medium. The addition of enzyme above this amount results only in its precipitation. However, unlike some compounds, enzymes are highly sensitive to their environment.

In the context of the present invention, the solubility of the enzyme is considered in absence of any stabilizing or reducing agent, particularly in absence of BSA and/or TCEP. It is inferred from the amount of protein lost due to precipitation after a period of time in a given environment, as well as predicted, based on the peptide sequence, by the Protein-Sol web server curated by Hebditch et al. 2017. The parent Endo V solubility is predicted to be 41% relative to the average solubility of the *E. coli* proteome. The variants of the invention advantageously exhibit a predicted increase in solubility of 5, 10, 15 and 20% under physiological conditions compared to the parent Endo V. The predicted increase in solubility is confirmed by the 20, 15, 10 and 5% lower percentage of Endo V lost due to precipitation In a particular embodiment, the variant of the invention comprises at least one substitution as compared to SEQ ID No 1 at position(s) selected K133, K138, K155 and K194 said variant exhibiting an increased thermostability and/or an increased solubility compared to the parent Endo V.

Particularly, the variant may comprise at least one substitution selected from K133T, K138D/Y, K155G/N and K194R, preferably selected from K133T, K138D and K194R.

In a particular embodiment, the variant comprises at least the substitution K133T. Interestingly, this variant exhibits an improved thermostability by 3 to 4° C. or more, compared to parent enzyme. The combination of substitutions K133T with at least one additional substitution selected from K138D/Y K155G/N and K194R advantageously improves the solubility of the enzyme.

Preferably, the variant comprises at least the substitution C169Q and one or more of the above listed substitutions.

In a particular embodiment, the variant comprises the combination of substitutions C169Q+K133T.

In a particular embodiment, the variant comprises the combination of substitutions C169Q+K133T+K138D/Y.

In a particular embodiment, the variant comprises the combination of substitutions C169Q+K138D/Y, preferably C169Q+K138D.

In a particular embodiment, the variant comprises the combination of substitutions C169Q+K155G/N, preferably C169Q+K155G.

In a particular embodiment, the variant comprises the combination of substitutions C169Q+K194R. In a particular embodiment, the variant comprises the combination of substitutions C169Q+K133T+K138D/Y+K155G/N+K194R, preferably C169Q+K133T+K138D+K194R. In a particular embodiment, the variant comprises a substitution on residue D206, preferably the substitution D206H. Substituting residue D206 for a histidine improved thermostability by 2° C. to 3° C. and increased the substrate affinity and catalytic rate by ~22 and ~38%, respectively, compared to the WT and while maintaining the stability profile of its parent (C169Q; Table 1). However, D206H decreases the ability of the enzyme to cleave a substrate that bears a fluorophore modification 3' proximal to the cleavage site.

In a particular embodiment, the variant comprises the combination of substitutions C169Q+D206H.

Interestingly, the inventors have discovered that combining mutations K133T, K138D/Y, and/or K155G/N onto a backbone that already carries C169Q and D206H generates an enzyme that has improved solubility properties, i.e. suffers less from precipitation (see Table 1). K133T, K138D/Y and K155G/N, each on their own may improve solubility. Advantageously, the combination of substitutions at these three K residues results in a dramatic improvement in solubility. Of note, other polar neutral or acidic amino acids may also fulfil this role at any of these three positions.

Therefore, in a particular embodiment, the variant comprises a combination of substitutions selected from C169Q+D206H+K133T, C169Q+D206H+K138D/Y, C169Q+D206H+K155G/N, C169Q+D206H+K133T+K138D/Y, C169Q+D206H+K133T+K155G/N.

In a preferred embodiment, the variant comprises the combination of substitutions C169Q+K133T+K138D+K155G+D206H.

Measurement of TdT Variant Stability

Increases in the stability of a protein may be measured in a variety of ways. Fluorescent-based thermal shift assays are particularly useful for such measurements because of their simplicity and low cost. Exemplary references describing thermal shift assays and their application to measuring protein stability are as follows: Pantoliano et al, J. Biomolecular Screening, 6(6): 429-440 (2001); Huynh et al, Curr. Protocol. Protein Science, 79: 28.9.1-28.9.14; Ericsson et al, Anal. Biochem., 357: 289-298 (2006); Niesen et al, Nature Protocols, 2(9): 2212-2221 (2007); and Pantoliano et al, U.S. Pat. No. 6,020,141, the latter of which is hereby incorporated by reference. The conceptual basis for such assays is that folded and unfolded proteins can be distinguished through exposure to a hydrophobic fluorescent probe. Such a probe is quenched in aqueous solution but will preferentially bind to the exposed hydrophobic interior of an unfolding protein leading to a sharp decrease in quenching so that a readily detected fluorescence emission can be studied as a function of temperature. Thermally induced unfolding is an irreversible unfolding process following a typical two-state model with a sharp transition between the folded and unfolded states, where melting temperature (Tm) is defined as the midpoint of temperature of the protein-unfolding transition. Melting temperatures obtained with such a so-called "thermofluor" method have been shown to correlate well for several proteins with values determined by other biophysical methods used for measuring protein stability, such as circular dichroism (CD), turbidity measurements, and differential scanning calorimetry.

Low fluorescence at room temperature indicates a well-folded protein. Fluorescence emission increases with increasing temperature, giving rise to a sigmoidal curve that represents cooperative unfolding of the protein. The resulting sigmoidal curves may be fit to a Boltzmann Equation to identify the melting temperature that occurs at the midpoint of the unfolding transition; alternatively, the Tm is easily identified by plotting the first derivative of the fluorescence emission as a function of temperature (−dF/dT), where the Tm corresponds to the minimum of the curve, Huynh et al (cited above).

A variety of fluorescent dyes may be used and are commercially available directly or as part of an assay kit. An exemplary fluorescent dye is SYPRO Orange. A conventional real-time PCR instrument may be used for temperature control and fluorescent detection. Typically, a selection of buffers, salt concentrations and compositions, and other additives is made that Nucleic Acids, Expression Cassette, Vector, Host Cell It is a further object of the invention to provide a nucleic acid encoding an Endo V variant as defined above.

The invention also encompasses nucleic acids which hybridize, under stringent conditions, to a nucleic acid encoding an Endo V variant as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding an Endo V variant of the invention, wherein the sequence of said nucleic acids, or a portion of said sequence at least, has been engineered using optimized codon usage. Alternatively, the nucleic acids according to the invention may be deduced from the sequence of the Endo V variant according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a control sequence such as transcriptional promoter and/or transcription terminator. The control sequence may include a promoter that is recognized by a host cell or an in vitro expression system for expression of a nucleic acid encoding an endonuclease V of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the Endo V variant. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide. Generally, the regulatory elements that are present in an expression vector include a transcriptional promoter, a ribosome binding site, a terminator, and optionally present operator. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be a eukaryotic cell, such as a yeast, fungal, mammalian, insect or plant cell.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation.

Optionally, more than one copy of a nucleic acid, cassette or vector of the present invention may be inserted into a host cell to increase production of the variant.

It is thus another object of the present invention to provide a method of producing an endonuclease V comprising:

(a) culturing the host cell according to claim 11 under conditions suitable to express the nucleic acid encoding the endonuclease V; and optionally (b) recovering said endonuclease V from the cell culture.

Use of the Endo V Variants of the Invention

It is a further object of the invention to provide methods using an Endo V variant of the invention that can be stored in the preferred reaction buffer for 2, 4, 6 or more days at 4° C. without the presence of stabilizing or reducing agents such as BSA and TCEP and without accruing more than 20, 40 or 60% loss in enzymatic activity due to their improved stability. Furthermore, the improved cleavage activity of the Endo V variants of the invention provide a method to specifically cleave single-stranded nucleic acid at the second phosphodiester bind 3' to a deoxyinosine residue and release a deoxyinosine-free single-stranded nucleic acid from a solid support, such as agarose beads, into solution in a 15, 30, 45, 60 or 75% shorter period of time compared to the WT Endo V. The nucleic acid may or may not contain a modified base bearing a fluorophore, quencher, biotin or other modifications immediately 3' to the second phosphodiester bond. One or more embodiments of the present invention provide compositions, methods and kits for various nucleic acid assays, wherein a variant of Endo V that is capable of nicking an inosine-containing strand of a single or double-stranded nucleic acid at a location 3' to the inosine residue is employed.

It is therefore an object of the present invention to provide a nucleic acid assay employing a variant of the present invention, as described above, comprising:

Providing a nucleic acid that is conjugated to a solid support at its 5' terminal and which contains an inosine residue;

Nicking the inosine-containing strand of the nucleic acid at the second phosphodiester bond 3' to the inosine residue using the variant of Endo V of the invention to release a nucleic acid into solution that is inosine-free; and Performing the nucleic assay.

According to the invention, the method may further comprise the step of:

Extending the nicked inosine-containing strand via a nucleic acid amplification reaction using a DNA polymerase, or Extending the nicked inosine-free strand via a nucleic acid amplification reaction using a DNA polymerase.

It is another object of the present invention to provide a nucleic acid assay employing a variant of the present invention, as described above, comprising:

Providing a nucleic acid that is conjugated to a solid support at its 5' terminal, which contains an inosine residue and which contains a modification such as a biotin or similar on the base of the second nucleotide 3' to the inosine residue;

Nicking the inosine-containing strand of the nucleic acid at the second phosphodiester bond 3' to the inosine residue using the variant of Endo V of the invention to release a nucleic acid into solution that is inosine-free and which contains a biotin at the 5' terminal; and Performing the nucleic assay.

According to the invention, the method may further comprise the step of:

Extending the nicked inosine-containing strand via a nucleic acid amplification reaction using a DNA polymerase, or Extending the nicked inosine-free strand, with a modification such as a biotin or similar at its 5' terminal, via a nucleic acid amplification reaction using a DNA polymerase and;

Capturing the newly synthesized nucleic acid that includes a 5' biotin on streptavidin beads.

It is another object of the present invention to provide a nucleic acid assay employing a variant of the present invention, as described above, comprising:

Providing a nucleic acid that is conjugated to a solid support at its 5' terminal, which contains an inosine residue and which contains a FRET fluorophore on the base of the second nucleotide 3' to the inosine residue and a FRET quencher at the 3' terminal of the nucleic acid;

Nicking the inosine-containing strand of the nucleic acid at the second phosphodiester bond 3' to the inosine residue using the variant of Endo V of the invention to release a nucleic acid into solution that is inosine-free and which contains a FRET fluorophore at the 5' terminal and a FRET quencher at the 3' terminal; and According to the invention, the method may further comprise the step of:

Utilizing the FRET fluorophore and quencher-containing nucleic acid as a probe in fluorescence-based assays such as TaqMan-based, real-time polymerase chain reaction or fluorescent in situ hybridization.

It is another object of the present invention to provide a nucleic acid assay employing a variant of the present invention, as described above, comprising:

Providing a target nucleic acid, advantageously conjugated to a solid support at the 5' terminal;

Providing a nucleic acid polymerase;

Providing a variant of Endo V of the present invention, that is capable of nicking an inosine-containing strand of a nucleic acid at the second phosphodiester bond 3' to the inosine residue;

Generating a free nucleic acid released from the bound target nucleic acid, wherein the nucleic acid is free of the inosine residue;

Nicking the inosine-containing strand employing the variant of Endo V to generate a nicked nucleic acid; and Performing a nucleic acid polymerase reaction on the nicked nucleic acid employing the nucleic acid polymerase.

The invention will also be described in further detail in the following examples, which are not intended to limit the scope of this invention, as defined by the attached claims.

Endo Vs of the invention may also be used in template-free enzymatic synthesis of a polynucleotide having a predetermined sequence, for example, as described in Creton, International patent publication WO2020/165137. Briefly, such synthesis may be performed by the following steps: a) providing an initiator having a deoxyinosine penultimate to a 3'-terminal nucleotide having a free 3'-hydroxyl; b) repeating cycles of (i) contacting under elongation conditions the initiator or elongated fragments having free 3'-O-hydroxyls with a 3'-O-blocked nucleoside triphosphate and a template-independent DNA polymerase so that the initiator or elongated fragments are elongated by incorporation of a 3'-O-blocked nucleoside triphosphate to form 3'-O-blocked elongated fragments, and (ii) deblocking the elongated fragments to form elongated fragments having free 3'-hydroxyls, until the polynucleotide is formed; and c) treating the polynucleotide with an endonuclease V of the invention to cleave the polynucleotide from the initiator. The above method may also include washing steps after the reaction, or extension, step, as well as after the de-blocking step.

A variety of template-independent DNA polymerases may be used in the above method. In some embodiments, such enzymatic synthesis employs a terminal deoxynucleotidyl transferase (TdT) variant that display increased incorporation activity with respect to 3'-O-modified nucleoside triphosphates, such as described in Champion et al, U.S. Pat.

No. 10,435,676 and 10,752,887; and International patent publication WO/2020/099451, which are incorporated herein by reference.

In some embodiments, reaction conditions for an extension or elongation step may comprising the following: 2.0 μM purified TdT; 125-600 μM 3'-O-blocked dNTP (e.g. 3'-O—$NH_2$-blocked dNTP); about 10 to about 500 mM potassium cacodylate buffer (pH between 6.5 and 7.5) and from about 0.01 to about 10 mM of a divalent cation (e.g. $CoCl_2$ or $MnCl_2$), where the elongation reaction may be carried out in a 50 μL reaction volume, at a temperature within the range RT to 45° C., for 3 minutes. In embodiments, in which the 3'-O-blocked dNTPs are 3'-O—$NH_2$-blocked dNTPs, reaction conditions for a deblocking step may comprise the following: 700 mM $NaNO_2$; 1 M sodium acetate (adjusted with acetic acid to pH in the range of 4.8-6.5), where the deblocking reaction may be carried out in a 50 μL volume, at a temperature within the range of RT to 45° C. for 30 seconds to several minutes.

Guidance in selecting 3'-O-blocking groups and corresponding de-blocking conditions for the above method may be found in the following references, which are incorporated by reference: U.S. Pat. Nos. 5,808,045; 8,808,988; International patent publication WO91/06678; and references cited below. In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino group. In particular embodiments, the cleaving reaction involves TCEP, a palladium complex or sodium nitrite.

As used herein, an “initiator” (or equivalent terms, such as, “initiating fragment,” “initiator nucleic acid,” “initiator oligonucleotide,” or the like) refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In one embodiment, the initiating fragment possesses between 3 and 100 nucleotides, in particular between 3 and 20 nucleotides. In one embodiment, the initiating fragment is single-stranded. In an alternative embodiment, the initiating fragment is double-stranded. In a particular embodiment, an initiator oligonucleotide synthesized with a 5'-primary amine may be covalently linked to magnetic beads using the manufacturer's protocol. Likewise, an initiator oligonucleotide synthesized with a 3'-primary amine may be covalently linked to magnetic beads using the manufacturer's protocol.

EXAMPLES

The present invention is described in more detail with reference to the following Examples. However, the invention should not be limited hereto.

Preparation of the Wild-Type Endo V gene

The nucleotide sequence of the nfi gene encoding the Endo V enzyme from *Escherichia coli* str. K-12 substr. MG1655 was obtained from the GenBank database at NCBI (GenBank Accession NC_000913.3). The nfi nucleotide sequence (SEQ ID No. 2) was codon optimized for expression and the base sequence was further adapted to include a nucleotide sequence encoding an amino-terminal HIS-tag sequence to facilitate purification of the protein (SEQ ID No. 1). The complete sequence was ordered from Integrated DNA Technologies (IDT) as a synthetic gene cloned into a pUC19 recombinant vector.

The codon optimized nfi gene was amplified from the pUC19 vector using a Phire Hot Start II DNA Polymerase PCR kit (ThermoFisher Scientific). The reaction was prepared as follows; 0.1 ng of the template DNA was combined with 200 μM dNTPs, 0.25 μM each of a forward and reverse oligonucleotide primer flanking the nfi gene containing restriction sites for NcoI and NotI, respectively, 8 μl PhireII HS Buffer and 0.4 μl PhireII HS polymerase and $H_2O$ to a final volume 40 μl.

The reaction was transferred to a Biometra TOne thermal cycler (Analytic Jena) that was programmed to execute the following cycles: 1) 98° C. for 30 seconds, 2) 98° C. for 5 seconds, 3) 55° C. for 15 seconds, 4) 72° C. for 60 seconds and 5) 72° C. for 5 minutes. Cycles 2 to 4 were repeated 35 times. 10% of the amplified product was visualized on a 1% agarose gel to ensure the correctly sized product was formed. The remainder of the amplified product was purified using a QAIquick PCR Purification kit (QAIgen).

To prepare the amplified nfi gene and pET28a(+) expression vector (Novagen) for cloning, 600 ng of each of the purified PCR product and pET28a(+) vector was cleaved separately with NcoI and NotI endonuclease restriction enzymes (NEB) for 1 hour at 37° C. in a final volume of 20 μl and containing the CutSmart reaction buffer (NEB). The cleaved products were purified using a QAIquick PCR Purification kit (QAIgen).

The nfi gene fragment and pET28a(+) vector fragments were combined for ligation by adding 1 ng of the nfi fragment and 110 ng vector fragment together with 1 μl T4 DNA ligase and 2 μl T4 DNA ligase buffer (NEB) in a 20 μl final volume. The ligation reaction was incubated overnight at 16° C.

One μl of the ligation reaction was transformed into E. Cloni® 10G Electrocompetent Cells (Lucigen) as described by the manufacturer Eporator electroporator (Eppendorf). The transformation mixture was spread onto 2×TY agar media (Sigma Aldrich) supplemented with 0.5% glucose and 50 $\mu g \cdot ml^{-1}$ kanamycin (Sigma Aldrich) and incubated overnight at 37° C. Transformed colonies containing the pET28-nf construct were inoculated into 2×TY growth media supplemented with 0.5% glucose and 50 $\mu g \cdot ml^{-1}$ kanamycin and incubated overnight at 37° C. while shaking at 260 RPM in an Innova Shaker.

The pET28-nfi plasmid DNA was extracted and purified from 5 ml of each of the E. cloni cultures using a QIAprep Spin Miniprep Kit (QAIgen). A sample of each plasmid preparation was sequenced by means of Sanger Sequencing at Biofidal (France) and the nucleotide sequence generated was verified against the original sequence in SEQ ID No 1.

Formation of the Endo V Variants

First prepared were site-specific mutants targeting the C136, C169 and C192 residues to improve enzyme stability. For each of the three loci, a single oligonucleotide primer was designed containing substitution bases at the position in the primer that corresponds to the codon of interest. Site-specific mutations were introduced into the wild-type nfi gene sequence using the megaprimer PCR protocol described described by Ke and Madison, 1997 and in detail below.

The most optimal variant from the aforementioned libraries, namely C169Q, was used as a backbone for successive variants to further improve the thermostability, solubility and cleavage properties of the enzyme. Residues identified as targets for site-specific mutagenesis to improve these properties on the C169Q backbone included, but was not limited to, K133, K138, K155, K194R and D206, due to their proximity to the DNA binding pocket of Endo V. The site-specific mutants were constructed following the megaprimer PCR protocol described in detail below.

The recombinant genes encoding active Endo V variants displaying improved thermostability, solubility and or cleavage rates were finally further combined in a combinatorial library to obtain variants with random combinations of beneficial mutations. The combinatorial library was constructed by following a staggered-extension PCR protocol to generate a megaprimer containing the randomly mixed alleles as described in detail below.

Megaprimer PCR Protocol for Mutant Generation

Megaprimers for mutant generation were generated as follows. The oligonucleotide primers targeting the loci to be mutated were each combined with the appropriate forward or reverse oligonucleotide primer flanking the nfi gene in the pET28a(+) vector.

The polymerase chain reactions included 1 ng of the pET28-nfi plasmid, 1 μM of oligonucleotide pair (0.5 μM per oligonucleotide) as primer, 200 μM dNTPs, 10 μl PhireII HS Buffer and 1 μl PhireII HS polymerase and $H_2O$ to a final volume 50 μl. The PCR reactions were transferred to a Biometra TOne thermal cycler that was programmed to execute the following cycles: 1) 98° C. for 30 seconds, 2) 98° C. for 6 seconds, 3) 55° C. for 10 seconds, 4) 72° C. for 15 seconds and 5) 72° C. for 5 minutes. Cycles 2 to 4 were repeated 30 times.

To generate megaprimers containing random combinations of mutations with known beneficial phenotypes, the selected plasmids bearing the mutant nfi genes were combined into a single tube at equimolar ratios. The mixed template DNA amplified in a staggered extension PCR reaction, as first described by Zhao and Zha (2006) using two oligonucleotide primers that flank the nfi genes in the pET28a(+) vector. A staggered extension PCR protocol facilitates allelic recombination of known mutations by employing shortened elongation steps.

The staggered extension polymerase chain reactions included 55 ng of the mixed mutant pET28-nfi plasmids combined with 1 μM each oligonucleotide pair (0.5 μM per oligonucleotide) as primer, 25 μl REDTaq ReadyMix™ PCR Reaction Mix and $H_2O$ to a final reaction volume of 50 μl. The PCR reactions were transferred to a Biometra TOne thermal cycler that was programmed to execute the following cycles: 1) 94° C. for 1 minute, 2) 94° C. for 30 seconds, 3) 55° C. for 30 seconds, 4) 72° C. for 10 seconds, 5) 94° C. for 30 seconds and 6) 72° C. for 1 minute. Cycles 2 to 4 were repeated 15 times before repeating cycles 5 and 6 20 times.

Following construction of the megaprimers by either of the two protocols described above, 10% of the amplified product was visualized on a 1% agarose gel to ensure the correctly sized products were formed. The remainder of the amplified products were purified using a QAIquick PCR Purification kit (QAIgen).

Each of the amplified PCR products containing the site-specific mutations or recombined alleles was used as a megaprimer to amplify the appropriate pET28-nfi plasmid encoding either the WT Endo V or Endo V with the C169Q substitution. 150 ng of each megaprimer was combined with 10 ng of the pET28-nfi plasmid, 200 μM dNTPs, 10 μl PhireII HS Buffer and 1 μl PhireII HS polymerase and $H_2O$ to a final volume 50 μl. The PCR reactions were transferred to a Biometra TOne thermal cycler that was programmed to execute the following cycles: 1) 98° C. for 30 seconds, 2) 98° C. for 7 seconds, 3) 72° C. for min and 4) 72° C. for 10 minutes. Cycle 3 was repeated 30 times.

Following PCR amplification, the original parental pET28-nfi plasmid DNA was degraded using the DpnI endonuclease restriction enzyme (NEB) that selectively cleaves methylated DNA. 10 μl DpnI buffer, 2 μl DpnI and 38 μl H2O was added to each reaction and incubated for 2 h at 37° C. in Biometra TOne thermal cycler. 10% of the amplified product was visualized on a 1% agarose gel to ensure the correctly sized products were formed. The remainder of the amplified products were purified using a QAIquick PCR Purification kit (QAIgen).

One μl of each of the DNA libraries was transformed into E. Cloni® 10G Electrocompetent Cells as described by the manufacturer using an Eporator electroporator. All of the transformation mixture from each library was spread onto 2×TY agar media (Sigma Aldrich) supplemented with 0.5% glucose (Sigma Aldrich) and 50 $\mu g \cdot ml^{-1}$ kanamycin (Sigma Aldrich) and incubated overnight at 37° C. The bacterial colonies for each library were scraped together with a spreader after adding 1 ml 2×TY per plate and mixed by vigorous shaking for 1 minute. The recombinant plasmid DNA was extracted from 1 ml of each mixture of cells using a QIAprep Spin Miniprep Kit.

The recombinant plasmid DNA libraries were transferred to the E. Cloni® EXPRESS BL21(DE3) protein expression strain by electroporation as described by the manufacturer using an Eporator electroporator. Dilutions of the transformation mixtures were spread onto 2×TY agar media supplemented with 0.5% glucose and 50 $\mu g \cdot ml^{-1}$ kanamycin and incubated overnight at 37° C. Single colonies were selected and inoculated into a 2 ml 96 well plate containing 600 μl 2×TY media supplemented with 0.5% glucose and 50 $\mu g \cdot ml^{-1}$ kanamycin and incubated for 16 hours at 37° C. in a Heidolph 1000 shaking incubator at 900 rpm. 65 μl of the grown cultures from each well of the 96 well plate were combined with 35 μl 70% glycerol in a new 200 μl 96 well plate and sealed for storage at −80° C. The cells from the remainder of each culture were collected by centrifugation and sent to Biofidal where the plasmid DNA was extracted and the mutant nfi genes sequenced by means of Sanger Sequencing to determine their genotype with reference to the original sequence in SEQ ID No 1.

Expression and Purification of the Wild-Type and Mutant Endo V

WT or mutant Endo V was expressed at small scale to assess their activity in crude lysate on a deoxyinosine-containing FRET substrate. 10 μl of the thawed stock cultures were inoculated into a 2 ml 96 well plate containing 600 μl 2×TY media supplemented with 0.5% glucose and 50 $\mu g \cdot ml^{-1}$ kanamycin and incubated for 16 hours at 37° C. in a Heidolph 1000 shaking incubator at 900 rpm. After growth, 50 μl of each culture was transferred to a new 2 ml 96 well plate containing 500 μl 2×TY agar media supplemented with 0.5% glucose and 50 $\mu g \cdot ml^{-1}$ kanamycin and incubated in a Heidolph 1000 shaking incubator at 900 rpm. After 2 hours incubation at 37° C., 50 μl 2×TY media supplemented with 6 mM isopropyl β-D-1-thiogalactopyranoside (IPTG, 0.5 mM final concentration) was added to each culture to induce expression of the Endo V from the pET28a(+) expression vector at 25° C. for 24 hours.

To obtain lysate containing the expressed Endo V, the cells from the expression cultures were collected by centrifugation in an Eppendorf Centrifuge 5920 R at 3428×g for 40 minutes. The cell pellets were frozen at −80° C. for at least 16 hours before being lysed in the presence of 300 μl lysis buffer (25 mM TRIS pH 8.5, 10 mM imidazole, 0.3% Triton 100, 1 mM $CaCl_2$), 1 μl·ml−1 DNAse I, 0.2 mg·ml−1 lysozyme, 1 mM DTT) for 2 h at 25° C. with vigorous shaking. Thereafter, 300 μl of a solution containing 1 M NaCl was added and incubated for an additional hour at 25° C. with vigorous shaking. The cell debris and insoluble protein was separated from the soluble protein by centrifugation at 3700 rpm for 40 min at 15° C. The lysates were transferred into a new 2 ml 96 well plate and stored at 4° C. prior to use.

WT Endo V and variants with better performance, was purified at a 50 ml culture scale from the stored E. Cloni® EXPRESS BL21(DE3) cultures as follows: 10 μl of the thawed stock culture was inoculated into a 5 ml 2×TY media supplemented with 0.5% glucose and 50 μg·ml$^{-1}$ kanamycin and incubated overnight at 37° C. while shaking at 260 RPM in an Innova Shaker. 500 μl of grown culture was transferred to a 250 ml Erlenmeyer flask containing 50 ml 2×TY agar media supplemented with 0.5% glucose and 50 μg·ml$^{-1}$ kanamycin, and incubated at 37° C. while shaking at 260 RPM in an Innova Shaker. When the optical density at 600 nm reached approximately 1, the culture was transferred to a similar incubator set at 25° C. and, after 1 hour of growth at 25° C., Endo V expression was induced with the addition of IPTG to a final concentration of 0.5 mM. After 24 hours of expression, the cells were harvested in a 50 ml conical tube by centrifugation in an Eppendorf Centrifuge 5920 R at 3400×g for 40 minutes.

The cell pellet was frozen at −80° C. for at least 16 hours before being lysed in the presence of 22.5 ml lysis buffer (25 mM TRIS pH 8.5, 0.3% Triton 100, 1 mM $CaCl_2$), 1 μl·ml$^{-1}$ DNAse I, 0.2 mg·ml−1 lysozyme, 1 mM DTT) for 2 h at 25° C. with vigorous shaking. Thereafter, 2.5 ml of a 5 M NaCl was added and incubated for an additional hour at 25° C. with vigorous shaking. The cell debris and insoluble protein was separated from the soluble protein by centrifugation at 3400×g for 40 min at 15° C.

The lysate was transferred into a new 50 ml conical tube and the His-tagged Endo V was captured using 100 μl equilibrated HisPur™ Ni-NTA Resin (ThermoScientific). After binding for 1 hour the entire mixture was filtered through a Bio-Spin Disposable Chromatography Column (Bio-Rad). Unwanted protein, salts and cellular components were washed away by step-wise applying 50 ml wash buffer (25 mM TRIS-Cl pH 8.5, 10 mM imidazole, 0.5 M NaCl) to the column over a custom vacuum unit set to 600 mBar. The purified Endo V was eluted from the Ni-NTA resin by applying 120 μl elution solution (25 mM TRIS-Cl pH 8.5, 300 mM imidazole, 0.5 M NaCl) and collecting the flow-through in a 1.5 ml microfuge tube by means of centrifugation at 2000×g in an Eppendorf Microfuge. This procedure generally yields a total of 800 μg or more of highly pure Endo V.

Production of DNA Substrate Conjugated to a Solid Support

To produce a deoxyinosine-containing oligonucleotide substrate bearing either a reporter fluorophore or FRET pair, oligonucleotides with the sequences presented in SEQ ID No 3, SEQ ID No 4 and SEQ ID No 5 and containing a 5'-amino for attachment were ordered from Integrated DNA Technologies (IDT). The oligonucleotides with the 5'-amino were conjugated to cyanogen bromide-activated (CnBr) resin (Sigma-Adrich) per manufacturer's instructions. The resin with the coupled deoxyinosine-containing oligonucleotide substrate was then equilibrated in a conventional Endo V cleavage buffer (e.g. NEBuffer4 (50 mM potassium acetate, 20 mM Tris-acetate, 10 mM magnesium acetate, 1 mM DTT ((New England Biolabs)).

Results

FIG. 1 shows that all the Endo V variants of the invention exhibited improved stability compared to the WT Endo V after 6h of incubation at stressful (42° C.) and non-stressful (4° C.) temperatures. Endo V C169Q served as the backbone for the E3, E4 and E5 variants that contain various combinations of mutations K133T, K138D, K155G, K194R and or D206H. E3 variant contains C169Q and D206H substitutions. E4 variant contains C169Q, K133T, K138D, K194R substitutions. E5 variant contains C169Q, K133T, K138D, K155G, D206H substitutions. Cleavage activity, also referred to as the cleavage rate or reaction velocity, was measured as the change in fluorescent units per second when Endo V cleaved a single-stranded DNA (ssDNA) substrate containing a FRET quencher and fluorophore pair 5' and 3' to a deoxyinosine base, respectively, and in which the ssDNA substrate is covalently conjugated at the 5' end to an agarose bead. Residual cleavage activity is the ratio of the cleavage rates measured after the enzymes were incubated for 6 hours at 42° C. vs 4° C. The sequence of the substrate is provided in SEQ ID No 3. The substrate and enzyme concentrations were 6 and 0.3 μM, respectively, in a preferred buffer. The reaction was monitored in a CLARIOstar Plus microplate reader (BMG Labtech) at 37° C. with intervals of shaking and non-shaking of 2 and 8 seconds, respectively, and a gain of 750. Number of replicates (n)=3.

Figure 2:
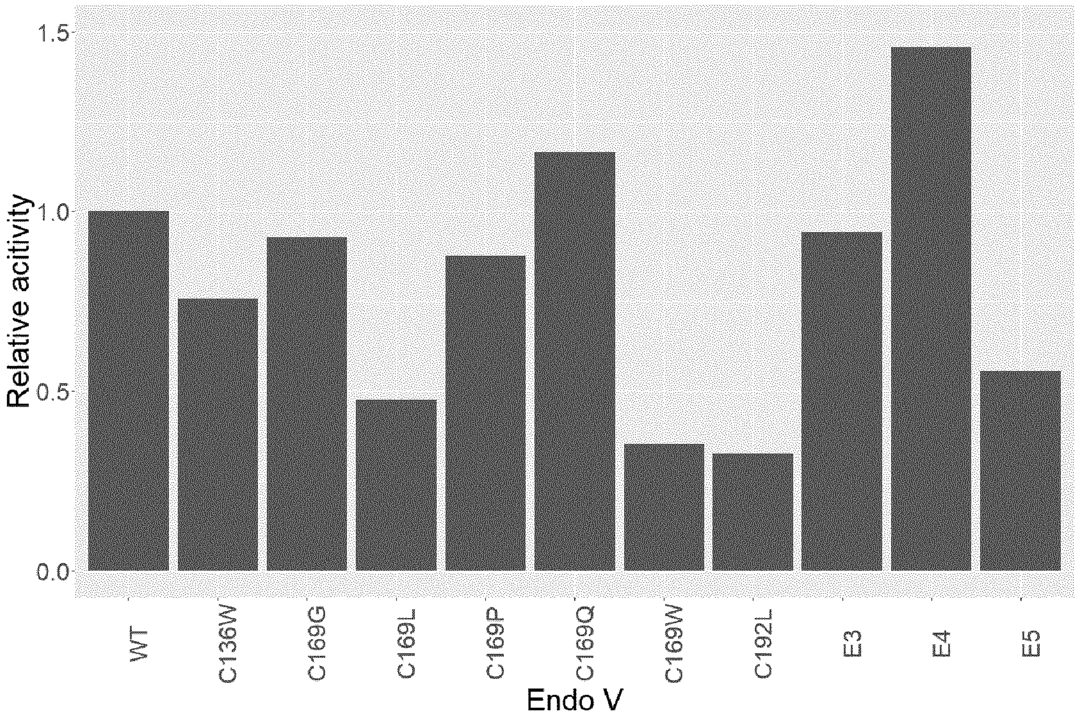
FIG. 2 shows the cleavage rates of the Endo V variants relative to the control in the absence of stabilizing agents.

FIG. 2 shows the cleavage rates of the Endo V variants relative to the control in the absence of stabilizing agents. While all the mutations indicated in FIG. 1 improve resistance to thermal stress, C169G, C169Q, E3 and E4 further exhibited a similar or improved cleavage rate compared to the WT Endo V. Endo V C169Q served as the backbone for the E3, E4 and E5 variants that contain various combinations of mutations K133T, K138D, K155G, K194R and or D206H. Cleavage activity, or initial reaction velocity, was measured as described in FIG. 1. Relative cleavage activity is the ratio of the cleavage rates of the Endo V variants to that of the WT Endo V. n=3.

Figure 3:
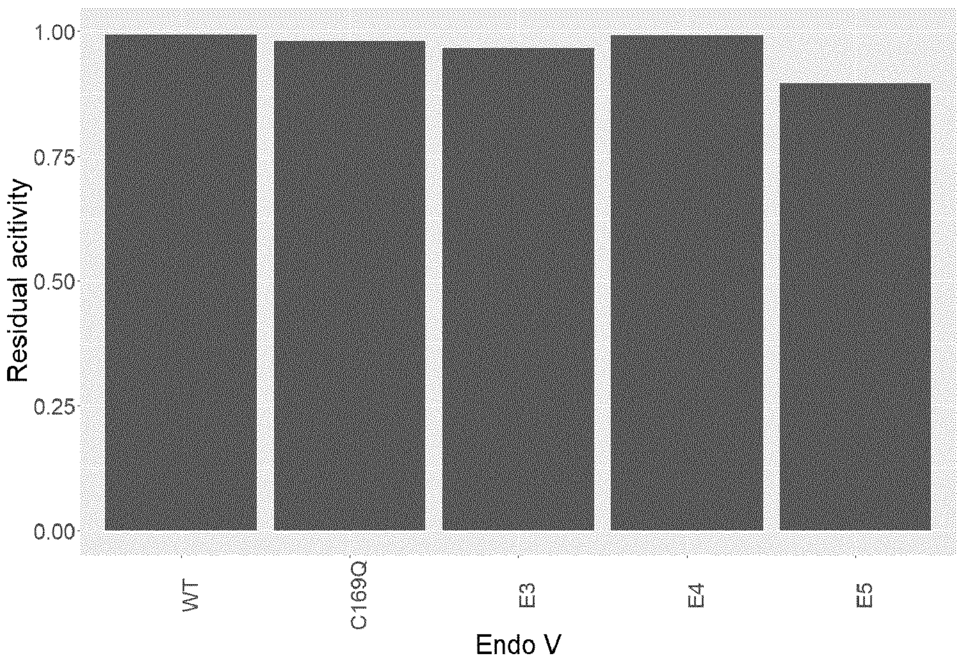
FIG. 3 is a graph showing that the C169Q substitution renders the use of stabilizing and reducing agents unnecessary for protecting the variants from losing activity during exposure to thermal stress at 42° C. for 6 hours.

FIG. 3 demonstrates that stabilizing and reducing agents such as BSA (0.033 mg·ml$^{-1}$) and TCEP (0.5 mM), respectively, can protect the WT Endo V from losing activity during exposure to thermal stress at 42° C. for 6 hours. FIG. 3 further demonstrates that the C169Q substitution renders the use of stabilizing and reducing agents unnecessary (also see FIG. 1). The control samples were incubated at 4° C. for the same duration. Endo V C169Q served as the backbone for the E3, E4 and E5 variants that contain various combinations of mutations K133T, K138D, K155G, K194R and or D206H. Residual cleavage activity was determined as described in FIG. 1. n=3.

Figure 4:
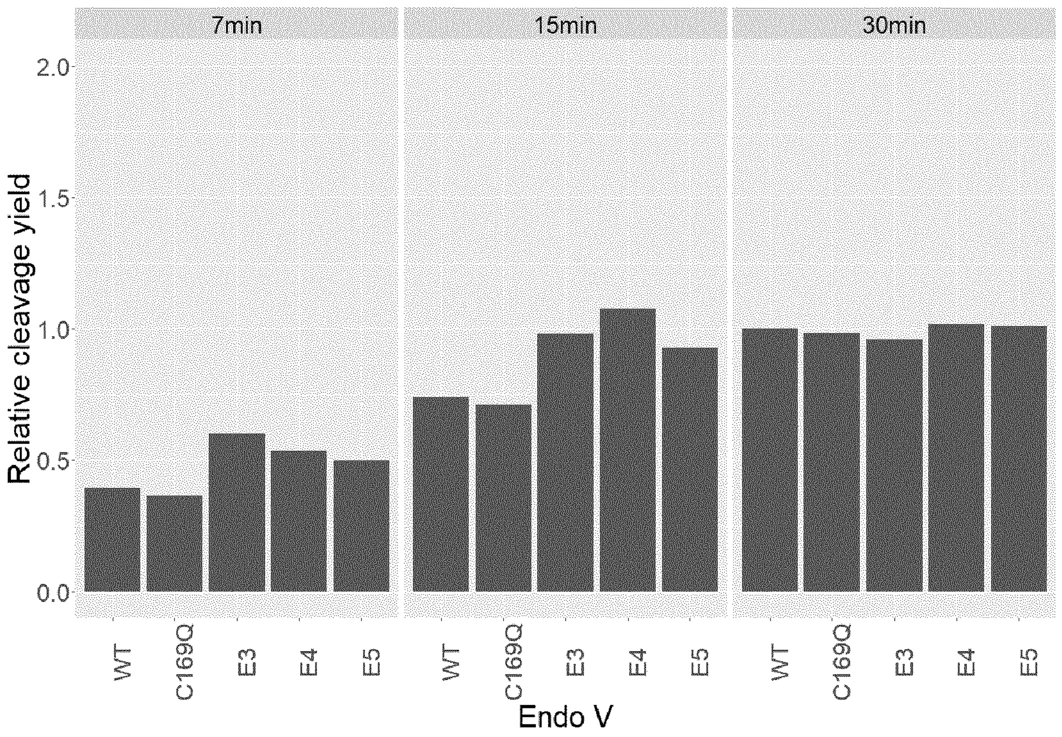
FIG. 4 is a graph showing the relative cleavage yield for Wild-type Endo V and various variants according to the present invention after the enzymes.

FIG. 4 demonstrates that variants E3, E4 and E5 can deliver the same amount of cleaved inosine-free nucleic acid from a solid support that what the WT Endo V yields in 30 minutes. Endo V C169Q served as the backbone for the E3, E4 and E5 variants that contain various combinations of mutations K133T, K138D, K155G, K194R and or D206H. All yields are presented relative to yield obtained by WT Endo V. The cleavage reaction took place in a 0.45 μm WWPTFE filter plate (PALL) and was incubated at 37° C. in a ThermoMixer C (Eppendorf) with shaking at 900 rpm. The fluorescently labelled oligonucleotide substrate (SEQ ID No 4) and Endo V enzyme concentrations were 6 and 0.3 μM, respectively, in a preferred buffer. The cleavage reactions were stopped after 7, 15 and 30 min with the addition of 0.2 M ethylenediaminetetraacetic acid (EDTA) and the cleaved product was collected from the filter plate in a collection plate by centrifugation at 2000×g for 2 minutes. The relative quantities were determined by measuring fluorescence in a CLARIOstar Plus plate reader. n=3.

Figure 5:
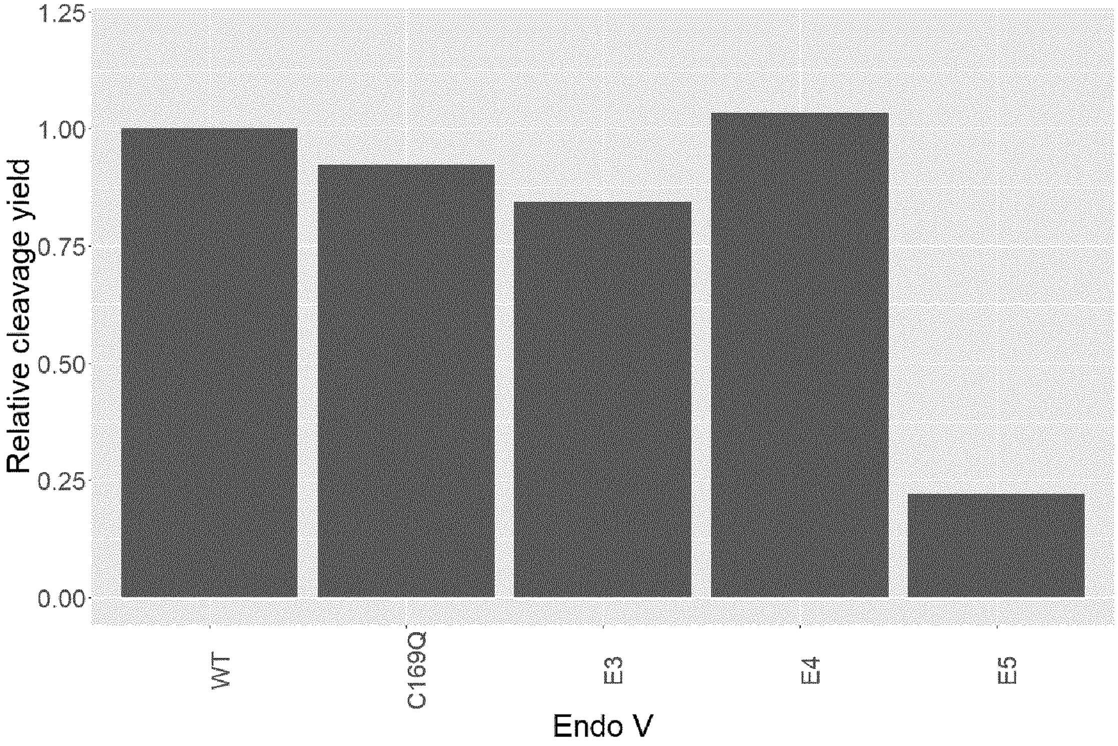
FIG. 5 is a graph showing the relative cleavage yields when a fluorescent moiety is linked to the base of the nucleotide proximal to the Endo V cleavage site (+1 position 3' to the deoxyinosine recognition site).

FIG. 5 reports the relative cleavage yields when a fluorescent moiety is linked to the base of the nucleotide proximal to the Endo V cleavage site (+1 position 3' to the deoxyinosine recognition site). It demonstrates that Endo V variant E4, in particular, retains the ability, similar to the WT Endo V, to cleave a substrate with a modified base located directly 3' to the cleavage site. The sequence of the oligonucleotide substrate conjugated to the solid support is provided by SEQ ID No 5. Endo V C169Q served as the backbone for the E3, E4 and E5 variants that contain various combinations of mutations K133T, K138D, K155G, K194R and or D206H. All yields are presented relative to the yield obtained after cleaving with the WT Endo V for 30 min. The reactions were carried out and cleavage yields were determined as described in FIG. 4. n=3.

TABLE 1

Kinetic, solubility and melting temperature properties of the Endo V mutants relative to the WT enzyme. Endo V C169Q served as the backbone for the E3, E4 and E5 variants that contain various combinations of mutations K133T, K138D, K155G, K194R and or D206H.

| Endo V | Relative yield after Ni-NTA purification [1] | Percentage protein lost due to precipitation after 4 days at 4° C.[2] | Percentage change in theoretical solubility[3] | Relative Km[4] | Relative Vmax[4] | Relative Kcat[4] | Relative Kcat/Km | Change in melting temperature [5] |
|---|---|---|---|---|---|---|---|---|
| WT | 1.00 | 18.90 | 0 | 1.00 | 1.00 | 1.00 | 1.00 | +0.0 |
| C169Q | 0.78 | 1.25 | 4.16 | 0.54 | 0.62 | 0.62 | 1.15 | +0.0 |
| E3 | 1.33 | 17.96 | 2.2 | 0.78 | 1.38 | 1.38 | 1.78 | +2.7 |
| E4 | 1.00 | ND[6] | 9.78 | 0.62 | 1.15 | 1.15 | 1.85 | +3.5 |
| E5 | 2.00 | 0.43 | 19.07 | 0.99 | 1.15 | 1.15 | 1.16 | +3.5 |

[1] The Endo V enzymes were expressed in *E. coli* BL21 for 24 h at 25° C. after induction with 0.5 mM isopropyl β-d-1-thiogalactopyranoside (IPTG) and purified from 50 ml culture in the presence of excess Ni-NTA. The protein concentration was determined by measuring absorbance at 280 nm. Protein yields are reported relative to the WT Endo V. n = 1.

[2] The percentage protein loss due to precipitation was calculated as the difference in protein concentration before and after storage of the protein eluate at 4° C. for 4 days. To separate the precipitated protein out of the solution, the eluate was centrifuged at 16000 × g for 10 min at 4° C. n = 1.

[3] Theoretical solubility was predicted from the peptide sequence using the Protein-Sol web tool hosted by Hebditch et al., (2017).

[4] To determine substrate affinity ($K_m$) and maximum reaction velocity ($V_{max}$), the initial reaction velocities of Endo V was determined by measuring the rate at which Endo V cleaved an oligonucleotide FRET substrate (SEQ ID No 3) conjugated to a solid support and presented to 0.2 uM Endo V at increasing concentration (187 nM to 24 μM) in a preferred buffer. The reaction was monitored in a CLARIOstar Plus microplate reader (BMG Labtech) at 37° C. with intervals of shaking and non-shaking of 2 and 8 seconds, respectively, and a gain of 750. n = 2.

[5] The protein melting temperatures (Tm) of the WT Endo V and the mutant derivatives are reported as the magnitude of the change in Tm relative to the WT Endo V. Tm was determined by means of a SYPRO Orange ™ thermal shift assay as per manufacturer's instructions. The protein concentrations were standardized to 4 μM and the change in fluorescence was monitored using a C1000 Touch Thermocycler (Bio-Rad) that was programmed to increase the temperature from 35 to 70° C. at increments of 0.5° C. · $s^{-1}$ n = 3.

[6] Not determined.

Sequence listing

```
SEQ ID No 1
   1 MDLASLRAQQ IELASSVIRE DRLDKDPPDL IAGADVGFEQ GGEVTRAAMV
     LLKYPSLELV
  61 EYKVARIATT MPYIPGELSE REYPALLAAW EMLSQKPDLV FVDGHGISHP
     RRLGVASHFG
 121 LLVDVPTIGV AKKRLCGKFE PLSSEPGALA PLMDKGEQLA WVWRSKARCN
     PLFIATGHRV
 181 SVDSALAWVQ RCMKGYRLPE PTRWADAVAS ERPAFVRYTA NOP*

SEQ ID No 2
   1 atggcaagca gtcatcatca ccaccatcac catcatagca gcggtagcga
     aaatctgtat
  61 tttcagagcg gtagcagcga tctggcaagc ctgcgtgcac agcagattga
     actggccagc
 121 agcgttattc gtgaagatcg tctggataaa gatccgcctg atctgattgc
     cggtgcagat
 181 gttggttttg aacaaggtgg tgaagttacc cgtgcagcaa tggttctgct
     gaaatatccg
 241 agcctggaac tggttgaata taaagttgca cgtattgcaa ccaccatgcc
     gtatattccg
 301 ggttttctga gctttcgtga atatccggca ctgctggcag catgggaaat
     gctgagccag
 361 aaaccggatc tggtttttgt tgatggtcat ggtattagcc atccgcgtcg
     tctgggtgtt
```

-continued

| Sequence listing |
|---|
| 421 gcaagccatt ttggtctgct ggttgatgtt ccgaccattg gtgttgccaa aaaacgtctg |
| 481 tgtggtaaat ttgaaccgct gagcagcgaa ccgggtgcac tggcaccgct gatggataaa |
| 541 ggtgaacagc tggcatgggt ttggcgtagc aaagcacgtt gtaatccgct gtttattgcc |
| 601 accggtcatc gtgttagcgt tgatagcgca ctggcctggg ttcagcgttg tatgaaaggt |
| 661 tatcgtctgc cggaaccgac acgttgggca gatgcagttg caagcgaacg tccggcattt |
| 721 gttcgttata ccgcaaatca gccgtaataa |
| SEQ ID No 3<br>/5AmMC12/TTTTTTTTT/i5-TAMK/TTTT/ideoxyI/AATT/iFluorT/TTTTTTGGAAGACTTGACTGCAAATA |
| SEQ ID No 4<br>/5AmMC12/TTTTTTTTT/ideoxyI/TTTT/iFluorT/ACAACCAAGAGGTGACAGCAGA |
| SEQ ID No 5<br>/5AmMC12/TTTTTTTTT/ideoxyI/T/iFluorT/TTTACAACCAAGAGGTGACAGCAGA |

The invention claimed is:

1. An endonuclease V variant that comprises an amino acid sequence that has at least 95% identity to the full length amino acid sequence of SEQ ID NO: 1, wherein said variant 1 comprises a substitution that corresponds to a substitution in the polypeptide of SEQ ID NO: 1 selected from the group consisting of C169Q, C169L, C169P and C169W, (ii) has a deoxyinosine-specific nucleic acid cleavage activity, and (iii) exhibits improved residual activity under non-reducing conditions as compared to the endonuclease V of SEQ ID NO: 1.

2. The endonuclease V variant of claim 1, wherein the variant comprises a substitution that corresponds to a substitution in the polypeptide of SEQ ID NO: 1 selected from the group consisting of C169Q, C169L, and C169P.

3. The endonuclease V variant of claim 1, wherein the variant comprises at least one substitution at one or more positions corresponding to positions in the polypeptide of SEQ ID NO: 1 selected from the group consisting of positions 133, 138, 155 and 206.

4. The endonuclease V variant of claim 3, wherein said variant comprises at least one substitution that corresponds to a substitution in the polypeptide of SEQ ID NO:1 selected from the group consisting of K133T, K138D, K138Y, K155G, K155N and D206H.

5. The endonuclease V variant of claim 1, wherein said variant comprises a substitution or a combination of substitutions that correspond to a substitution or combination of substitutions in the polypeptide of SEQ ID NO: 1 selected from the group consisting of C169Q, C169Q+K133T, C169Q+K138D/Y, C169Q+K155G/N, C169Q+D206H, C169Q+K133T+K138D+K194R, and C169Q+K133T+K138D+K155G+D206H.

6. A method of cleaving a nucleic acid, wherein said method comprises contacting the nucleic acid with the endonuclease V variant of claim 1.

7. The method of claim 6, wherein the nucleic acid is a single stranded nucleic acid conjugated to a solid support.

8. The endonuclease V variant of claim 2, wherein the variant comprises a substitution that corresponds to a substitution in the polypeptide of SEQ ID NO: 1 selected from the group consisting of C169Q and C169L.

9. The endonuclease V variant of claim 8, wherein the variant comprises the substitution that corresponds to the substitution C169Q in the polypeptide of SEQ ID NO:1.

10. The endonuclease V variant of claim 4, wherein said variant comprises at least one substitution that corresponds to a substitution in the polypeptide of SEQ ID NO: 1 selected from the group consisting of K133T, K138D, K155G, and D206H.

* * * * *

SEQUENCE LISTING

<160> NUMBER OF SEQ ID NOS: 5

<210> SEQ ID NO 1
<211> LENGTH: 223
<212> TYPE: PRT
<213> ORGANISM: Escherichia coli

<400> SEQUENCE: 1

```
Met Asp Leu Ala Ser Leu Arg Ala Gln Gln Ile Glu Leu Ala Ser Ser
1               5                   10                  15

Val Ile Arg Glu Asp Arg Leu Asp Lys Asp Pro Pro Asp Leu Ile Ala
            20                  25                  30

Gly Ala Asp Val Gly Phe Glu Gln Gly Gly Glu Val Thr Arg Ala Ala
        35                  40                  45

Met Val Leu Leu Lys Tyr Pro Ser Leu Glu Leu Val Glu Tyr Lys Val
    50                  55                  60

Ala Arg Ile Ala Thr Thr Met Pro Tyr Ile Pro Gly Phe Leu Ser Phe
65                  70                  75                  80

Arg Glu Tyr Pro Ala Leu Leu Ala Ala Trp Glu Met Leu Ser Gln Lys
                85                  90                  95

Pro Asp Leu Val Phe Val Asp Gly His Gly Ile Ser His Pro Arg Arg
            100                 105                 110

Leu Gly Val Ala Ser His Phe Gly Leu Leu Val Asp Val Pro Thr Ile
        115                 120                 125

Gly Val Ala Lys Lys Arg Leu Cys Gly Lys Phe Glu Pro Leu Ser Ser
    130                 135                 140

Glu Pro Gly Ala Leu Ala Pro Leu Met Asp Lys Gly Glu Gln Leu Ala
145                 150                 155                 160

Trp Val Trp Arg Ser Lys Ala Arg Cys Asn Pro Leu Phe Ile Ala Thr
                165                 170                 175

Gly His Arg Val Ser Val Asp Ser Ala Leu Ala Trp Val Gln Arg Cys
            180                 185                 190

Met Lys Gly Tyr Arg Leu Pro Glu Pro Thr Arg Trp Ala Asp Ala Val
        195                 200                 205
```

```
Ala Ser Glu Arg Pro Ala Phe Val Arg Tyr Thr Ala Asn Gln Pro
    210                 215                 220


<210> SEQ ID NO 2
<211> LENGTH: 750
<212> TYPE: DNA
<213> ORGANISM: Artificial Sequence
<220> FEATURE:
<223> OTHER INFORMATION: Optimized nfi nucleotide sequence

<400> SEQUENCE: 2

atggcaagca gtcatcatca ccaccatcac catcatagca gcggtagcga aaatctgtat      60

tttcagagcg gtagcagcga tctggcaagc ctgcgtgcac agcagattga actggccagc     120

agcgttattc gtgaagatcg tctggataaa gatccgcctg atctgattgc cggtgcagat     180

gttggttttg aacaaggtgg tgaagttacc cgtgcagcaa tggttctgct gaaatatccg     240

agcctggaac tggttgaata taaagttgca cgtattgcaa ccaccatgcc gtatattccg     300

ggttttctga gctttcgtga atatccggca ctgctggcag catgggaaat gctgagccag     360

aaaccggatc tggtttttgt tgatggtcat ggtattagcc atccgcgtcg tctgggtgtt     420

gcaagccatt ttggtctgct ggttgatgtt ccgaccattg gtgttgccaa aaaacgtctg     480

tgtggtaaat ttgaaccgct gagcagcgaa ccgggtgcac tggcaccgct gatggataaa     540

ggtgaacagc tggcatgggt ttggcgtagc aaagcacgtt gtaatccgct gtttattgcc     600

accggtcatc gtgttagcgt tgatagcgca ctggcctggg ttcagcgttg tatgaaaggt     660

tatcgtctgc cggaaccgac acgttgggca gatgcagttg caagcgaacg tccggcattt     720

gttcgttata ccgcaaatca gccgtaataa                                      750


<210> SEQ ID NO 3
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: AmMC12
<220> FEATURE:
<221> NAME/KEY: misc_feature
<222> LOCATION: (11)..(11)
<223> OTHER INFORMATION: i5-TAMK
<220> FEATURE:
<221> NAME/KEY: misc_feature
<222> LOCATION: (15)..(15)
<223> OTHER INFORMATION: 2'-deoxyinosine
<220> FEATURE:
<221> NAME/KEY: misc_feature
<222> LOCATION: (20)..(20)
<223> OTHER INFORMATION: iFluorT

<400> SEQUENCE: 3

tttttttttt ttttnaattt ttttttggaa gacttgactg caaata                     46


<210> SEQ ID NO 4
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: AmMC12
```

-continued

```
<220> FEATURE:
<221> NAME/KEY: misc_feature
<222> LOCATION: (11)..(11)
<223> OTHER INFORMATION: 2'-deoxyinosine
<220> FEATURE:
<221> NAME/KEY: misc_feature
<222> LOCATION: (16)..(16)
<223> OTHER INFORMATION: iFluorT

<400> SEQUENCE: 4

ttttttttt ntttttacaa ccaagaggtg acagcaga                    38


<210> SEQ ID NO 5
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: AmMC12
<220> FEATURE:
<221> NAME/KEY: misc_feature
<222> LOCATION: (11)..(11)
<223> OTHER INFORMATION: 2'-deoxyinosine
<220> FEATURE:
<221> NAME/KEY: misc_feature
<222> LOCATION: (13)..(13)
<223> OTHER INFORMATION: iFluorT

<400> SEQUENCE: 5

ttttttttt ntttttacaa ccaagaggtg acagcaga                    38
```